United States Patent [19]

Bull

[11] 4,188,400

[45] Feb. 12, 1980

[54] FURYLMETHYLOXIME ETHERS

[75] Inventor: Michael J. Bull, Lower Halstow, England

[73] Assignee: Shell Oil Company, Houston, Tex.

[21] Appl. No.: 29,172

[22] Filed: Apr. 12, 1979

[30] Foreign Application Priority Data

May 18, 1978 [GB] United Kingdom ............... 20510/78

[51] Int. Cl.$^2$ ...................... C07D 307/52; A01N 9/20
[52] U.S. Cl. ................................... 424/285; 260/347.7
[58] Field of Search ...................... 260/347.7; 424/285

[56] References Cited

U.S. PATENT DOCUMENTS

| | | | |
|---|---|---|---|
| 3,946,049 | 3/1976 | Pelosi | 260/347.7 |
| 4,007,227 | 2/1977 | Baker et al. | 260/347.7 |
| 4,052,194 | 10/1977 | Wilcox | 260/347.7 |

OTHER PUBLICATIONS

Bestmann et al., Chem. Abst., 1966, vol. 65, col. 13749.
Breuer et al., Chem. Abst., 1964, vol. 60, col. 11870.
Sekuur et al., Chem. Abst., 1967, vol. 66, No. 15320r.

*Primary Examiner*—Natalie Trousof

[57] ABSTRACT

Certain benzyl-substituted furylmethyl oxime ethers, useful as insecticides.

4 Claims, No Drawings

FURYLMETHYLOXIME ETHERS

DESCRIPTION OF THE INVENTION

It has been found that compounds of the formula:

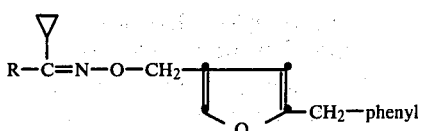

(I)

wherein R is naphthyl, phenyl, halophenyl, alkylphenyl or alkoxyphenyl, exhibit useful insecticidal activity.

In these compounds, each alkyl moiety preferably contains from one to four carbon atoms, and suitably is of either straight-chain or branched-chain configuration. By "halogen" is meant fluorine, chlorine and bromine. When substituted, it is preferred that the phenyl moiety is substituted at the para-position of the ring.

The compounds of Formula I exhibit geometric isomerism about the oximic double bond, and the present invention includes the individual E- and Z-isomers and mixtures thereof.

The compounds of Formula I can be prepared by reacting an alkali metal salt of a ketoxime of the general formula

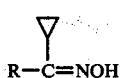

(II)

wherein R has the meaning given for Formula I, with a compound of the general formula

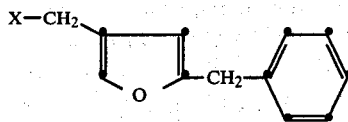

(III)

wherein X represents a chlorine, bromine or iodine atom, preferably a chlorine or a bromine atom, especially a chlorine atom.

The reaction is preferably carried out in the presence of a polar aprotic solvent. Particularly suitable solvents are anhydrous acetonitrile, dimethylformamide in toluene, or tetrahydrofuran. Reaction temperatures in the range 60°–150° C., preferably in the range 90°–110° C., and reaction times of 2 to 10 hours, may be used. Alternatively, the reaction may be carried out in a two-phase organic/inorganic system in the presence of a phase transfer catalyst. The phase transfer catalyst may be any reagent which will accelerate interphase reactions in organic/inorganic two-phase systems. The alkali metal salt of the ketoxime of formula II may be prepared by the reaction of an alkali metal hydride, for example sodium hydride, with the ketoxime, or by reaction of aqueous potassium or sodium hydroxide with the ketoxime. The alkali metal salt of the ketoxime is preferably prepared in situ.

The compounds of the general Formula III may be prepared by the reaction of 2-benzyl-4-hydroxymethylfuran with a suitable halogenating agent, for example thionyl chloride, suitably in an inert solvent in the presence of a base, for example pyridine.

The compounds of the invention have exhibited pesticidal, especially insecticidal, activity. The invention therefore provides a pesticidal composition which comprises as active ingredient a compound of the general Formula I, together with a suitable carrier. The invention also provides a method of combating pests at a locus, which comprises applying to that locus a compound of the general Formula I or a pesticidal composition according to the invention. The invention further provides the use of a compound of the general Formula I as a pesticide.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally, granules will contain ½–25% by weight toxicant and 0–1% by weight of additives such as stabilizers, slow release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight toxicant, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

The method of applying the products of this invention to control insects comprises applying the product, ordinarily in a composition of one of the aforementioned types, to a locus or area to be protected from the insects, such as the foliage and/or the fruit of plants. The product of course is applied in an amount sufficient to exert the desired action. This dosage is dependent upon many factors, including the carrier employed, the method and conditions of the application, whether the formulation is present at the locus in the form of an aerosol, or as a film, or as discrete particles, the thickness of film or size of particles, and the like, proper consideration and resolution of these factors to provide the necessary dosage of active material at the locus to be protected being within the skill of those versed in the art. In general, however, the effective dosage of products of this invention at the locus to be protected—i.e., the dosage which the insect contacts—is of the order of 0.001 to 0.5% based on the total weight of the formulation, though under some circumstances the effective concentration will be as little as 0.0001% or as much as 2%, on the same basis.

The following examples describe the preparation of individual species of the compounds of the invention in particular instances. In each case, the identity of the product was confirmed by appropriate elemental and spectral analyses.

EXAMPLE 1

Preparation of cyclopropyl-4-chlorophenyl ketoxime 2-benzyl-4-furylmethyl ether (1)

A solution of 13 g of thionyl chloride in toluene was added dropwise over 15 minutes to a mixture of 15.8 g pyridine and 18.8 g 2-benzyl-4-hydroxymethylfuran, in toluene, at a temperature of 0°–5° C. The mixture was slowly warmed to 80° C. and stirred for 1½ hours and then cooled in an ice-bath, poured into ice and filtered. The resulting solution was extracted with diethyl ether, washed with water and then with sodium bicarbonate solution, and dried over magnesium sulphate. The solution was then stripped of solvent, yielding a brown oil, which was chromatographed over silica gel using toluene as eluent to give 2-benzyl-4-chloromethylfuran (1A) as a brown oil.

A solution of 2.0 g of 4-chlorophenyl-cyclopropyl ketoxime in 20% by volume of a mixture of dimethylformamide and toluene was added dropwise to 1.0 g of a 50% suspension of sodium hydride in oil, over 15 minutes at a temperature of 90°–100° C. A solution of 2.2 g of 1A in 20% by volume dimethylformamide/toluene was added and the resulting mixture was stirred at 100° C. for 3 hours. The mixture was then cooled to room temperature, methanol was added to destroy the excess sodium hydride and the mixture was then poured onto ice in dilute hydrochloric acid, extracted with diethyl ether, washed with water and then with sodium bicarbonate solution and dried over magnesium sulphate. The solvent was stripped to yield a brown oil, which was then chromatographed over silica gel using 1:1 v/v hexane/methylene chloride as eluent to give 1, refractive index $\mu_D^{21} = 1.5905$.

EXAMPLE 2

The following further compounds of Formula I were prepared by the procedure described in Example 1.

(a) cyclopropyl-4-methoxyphenyl ketoxime 2-benzyl-4-furylmethyl ether (2), refractive index $\mu_D^{21} = 1.578$.

(b) cyclopropyl-4-fluorophenyl ketoxime 2-benzyl-4-furylmethyl ether (3), refractive index $\mu_D^{21} = 1.568$.

(c) cyclopropyl-4-t-butylphenyl ketoxime 2-benzyl-4-furylmethyl ether (4), refractive index $\mu_D^{24} = 1.568$.

The insecticidal activity of the compounds according to the present invention was assessed employing the following pests:

Insects: housefly, *Musca domestica* (M.d.) Egyptian spotted leafworm, *Spodoptera littoralis* (S.l.) corn earworm, *Heliothis zea* (H.z.)

The test methods employed for each species appear below:

(i) Housefly

A 0.4% by weight solution in acetone of the compound to be tested was prepared and taken up in a micrometer syringe. Two to three day old adult female houseflies were anaesthetized with carbon dioxide, and 1 l of the test solution was applied to the ventral side of the abdomen of each fly, 20 flies being tested. The treated flies were held in glass jars covered with paper tissue held by an elastic band. Cotton-wool pads soaked in dilute sugar solution were placed on top of the tissue as food. After 24 hours the percentage of dead and moribund flies was recorded.

(ii) Cotton leafworm

Pairs of leaves were removed from broad bean plants and placed on filter paper inside plastic petri dishes. The leaves were sprayed on the undersurface with a formulation containing 20% by weight of acetone, 0.05% by weight of TRITON X-100 (Trademark) as wetting agent and 0.4% by weight of the compound to be tested. Varying concentrations were obtained by diluting the formulation. After spraying the leaves were left for ½-1 hour drying period and then each leaf pair was infested with ten larvae of the Egyptian cotton leafworm. After 24 hours the percentage of dead and moribund larvae were recorded.

(iii) Corn earworm

A 0.2% by weight solution of the compound to be tested was prepared by adding 2 ml of a 1% acetone solution to 8 ml of 0.05% ATLOX 1045A (Trademark) solution. The cut broad bean plant was sprayed with 4 ml of test solution using a hand sprayer. Immediately after spraying, 5 larvae of the corn earworm were transferred to each plant which was inserted into water through the center hole of a test board and covered with a wire screen. 44–46 hours after spraying, the percentage of dead and moribund larvae was recorded.

In all of the tests, corresponding formulations of parathion were tested for comparison.

The results are shown in the following table in which the test species are identified by the initials noted above and the activity of each compound is expressed in the form of a Toxicity Index (T.I.) which is calculated from the following equation:

$$\text{Toxicity Index } (T.I.) = \frac{LC_{50} \text{ of parathion}}{LC_{50} \text{ of test compound}}$$

wherein $LC_{50}$ is the lethal concentration required to kill 50% of the test insect species.

| Group R in Test Compound Referring to Formula I | Toxicity Index | | |
|---|---|---|---|
| | M.d. | S.l. | H.z. |
| 4-chlorophenyl | 370 | | 313 |
| 4-methoxyphenyl | 6.5 | 9 | |
| 4-fluorophenyl | 260 | 136 | |
| 4-tert-butylphenyl | 21 | 14 | |

I claim:
1. A compound of the formula

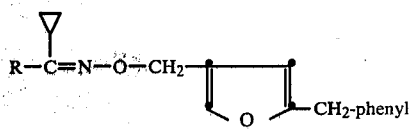

wherein R is naphthyl, phenyl, halophenyl, or alkylphenyl or alkoxyphenyl wherein the alkyl moiety contains from one to four carbon atoms.

2. A compound according to claim 1 wherein any substitutent on the phenyl moiety represented by R is bonded to the ring at the paraposition.

3. An insecticidal composition which comprises an effective amount of a compound of claim 1 together with an adjuvant therefor.

4. A method for protecting plants from attack by insects which comprises applying to the plants to be protected an effective dosage of a compound of claim 1.

* * * * *